United States Patent [19]

Aliotta et al.

[11] 3,997,330

[45] Dec. 14, 1976

[54] DENTAL AMALGAMS

[75] Inventors: Joseph Aliotta, Staten Island; Louis F. Alcuri, Brooklyn, both of N.Y.

[73] Assignee: Engelhard Minerals & Chemicals Corporation, Murray Hill, N.J.

[22] Filed: Dec. 29, 1975

[21] Appl. No.: 644,871

[52] U.S. Cl. .............................. 75/.5 R; 75/134 N; 75/169; 75/173 C

[51] Int. Cl.² .......................................... C22C 7/00

[58] Field of Search ............ 75/.5 R, 173 C, 134 N, 75/134 C, 169, 173 R

[56] References Cited

UNITED STATES PATENTS

| | | | |
|---|---|---|---|
| 1,963,085 | 6/1934 | Gray | 75/173 C |
| 2,281,991 | 5/1942 | Poetschke | 75/173 C |
| 3,305,356 | 2/1967 | Youdelis | 75/173 C X |
| 3,841,860 | 10/1974 | Wolf | 75/.5 R |
| 3,871,876 | 3/1975 | Asgar et al. | 75/169 |
| 3,933,961 | 1/1976 | Burns | 75/169 X |
| 3,954,457 | 5/1976 | Weikel | 75/169 |

*Primary Examiner*—L. Dewayne Rutledge
*Assistant Examiner*—E. L. Weise

[57] ABSTRACT

An improved dental composition comprises an admixture in specified proportions of two powdered alloys of specified composition, one in the form of spheres, the other in the form of irregularly-shaped particles such as flakes. When the admixture is amalgamated with mercury, a corrosion-resistant dental amalgam having enhanced mechanical properties and handling characteristics is produced.

7 Claims, 3 Drawing Figures

DENTAL AMALGAMS

This invention relates to improved dental amalgam compositions and to their preparation. More specifically it relates to a uniform admixture in designated proportions of two powdered alloys of specified composition and configuration, i.e., spheroids and irregularly-shaped particles which when amalgamated with mercury exhibits enhanced properties.

BACKGROUND

Dental amalgams are produced by intimately combining mercury with dental amalgam alloys, conventional of which are comprised generally of from about 67–72% by weight of silver, 25–27% tin, 0–5% copper and 0–2% zinc. Upon reaction with mercury using known dental clinical techniques, a plastic mass is produced which quickly sets into a hard rigid body. While the mass is plastic, it may be packed into a surgically prepared tooth restoring its anatomy and function.

The products of the amalgamation reaction are believed to be a silver-mercury reaction product ($Ag_2Hg_3$) and a tin-mercury reaction product ($Sn_{7-8}Hg$), referred to in the art as gamma-1 and gamma-2, respectively. It has been recognized that the presence of gamma-2 in dental amalgams is a source of corrosion in a saline environment. It is believed that the corrosion process probably releases mercury as a reaction product, resulting in the formation of additional voids and porosities. these may extend well below the surface since the gamma-2 phase in dental amalgam is interconnected. The excess mercury, voids and porosities serve to weaken the dental amalgam especially at the margins which are the interfaces between the restoration and tooth. As a consequence of normal occlusion, stresses generated at a weakened margin may destroy its integrity, allowing leakage of oral fluids and bacteria, thereby promoting secondary decay.

Regardless of whether the aforementioned explanation of the corrosion process due to the presence of gamma-2 is correct (and the present invention is not necessarily limited thereto), it has been found that corrosion can be reduced by techniques which minimize, inhibit or eliminate gamma-2 from dental amalgam compositions. U.S. Pat. No. 3,305,356, for example, discloses the preparation of dental amalgams by mechanically dispersing a hard, strong metal alloy comprising copper and silver throughout a conventional amalgam in the form of very fine particles. There is evidence that in such compositions some of the copper from the dispersed silver-copper alloy combines with tin, thereby inhibiting gamma-2 formation. This is not effective immediately, however, since the copper must first diffuse through a reaction zone which forms around the dispersant. From a corrosion standpoint the gamma-2 is eliminated over a period of weeks after initial trituration and condensation.

Inhibition of gamma-2 has also been attempted by use of silver-tin alloys containing about 5% gold. While the formation of gamma-2 may be somewhat inhibited in such alloys, the resulting gold-tin phase that forms is also subject to saline corrosion. Moreover, the amount of gold required to eliminate gamma-2 completely makes such dental amalgams expensive.

Similarly, for a number of years some dentists have been adding empirical amounts of copper-mercury (copper amalgam) to already triturated conventional amalgam. This procedure produces a good clinical amalgam the structure of which appears to contain little or no gamma-2 phase immediately after trituration. The disadvantage of this technique is that the copper amalgam is heated until mercury beads at its surface prior to mixing. This presents a substantial mercury hazard to the dental personnel and perhaps to the patient.

Other approaches, which may employ high copper content compositions, are disclosed, for example, in U.S. Pat. Nos. 2,281,991 and 3,871,876. In the former a mixture of two comminuted alloys are employed, one, however, being a preformed hardened silver amalgam rich in silver and mercury, which requires special handling procedures. In the latter, advantageous results are reported for an amalgamable silver alloy powder, wherein each particle has a gradient composition from exterior to interior, a characteristic requiring special manufacturing techniques.

Still other approaches have met with some success in minimizing or eliminating the gamma-2 phase, but with undesired side effects. For example, some otherwise successful compositions require increased amounts of mercury for amalgamation of the alloy.

Another approach is that set forth in companion patent application of Greener et al. entitled "Dental Amalgams", filed contemporaneously herewith. This approach involves an admixture of two powdered alloys, which when amalgamated with mercury produces a virtually gamma-2-free amalgam having improved corrosion resistance. Enhancement of handling and mechanical properties, however, is lacking and would be desirable.

OBJECTS OF THE INVENTION

It is a general object of this invention to provide dental amalgam compositions which cope with the aforementioned problems of other amalgams.

It is a specific object to provide high-copper-content dental amalgamable compositions which are substantially free of mercury prior to amalgamation and which can be readily amalgamated without undue risks to personnel resulting from excessive mercury exposure.

It is another specific object to provide new dental amalgam compositions which upon amalgamation with mercury do not unduly form the gamma-2 phase and which provide both enhanced mechanical and electrochemical properties.

It is another specific object to provide dental amalgam compositions which upon amalgamation with mercury substantially immediately inhibit gamma-2 formation so as to be substantially free of the gamm-2 phase.

It is another specific object to provide a dental composition having desired handling properties and which is competitive in cost with other amalgam compositions.

It is another specific object to provide an amalgamable dental composition which can be prepared or manufactured employing conventional techniques.

It is another specific object to provide dental amalgam compositions having improved properties upon amalgamation without unduly increasing the amounts of mercury required in the preparation thereof.

These and other objects will become apparent as the detailed description proceeds.

DESCRIPTION OF THE INVENTION

The new and improved dental amalgam compositions of this invention comprise an admixture of the same two powdered alloys disclosed in the aforementioned Greener et al. application, hereinafter referred to as Alloy No. 1 and Alloy No. 2, respectively. To achieve enhanced mechanical properties without sacrifice of improved corrosion resistance, however, Alloy No. 1 is present as a major proportion in the form of spheroidal particulates and Alloy No. 2 is present as a minor proportion in the form of irregularly-shaped particulates. The presence of the two alloys in the forms and proportions indicated provide the unexpected advantages although the mechanism thereof is not fully understood.

Alloy No. 1 is comprised of silver, tin and copper with silver present in the range of about 40% to 70% by weight, tin in the range of about 10% to 30% by weight and copper in the range of about 20% to 40% by weight. Alloy No. 2 is comprised of silver, tin, copper and zinc with silver present in the range of about 55% to 75% by weight, tin in the range of about 20% to 40% by weight, copper in the range of about 0.05% to 10% by weight and zinc in the range of about 0.1% to 2.0% by weight.

As already set forth, Alloy No. 1 is present as a major proportion of the powdered admixture, i.e., more than about 50% by weight, e.g., about 55% to about 90% of the composition by weight, optimally about 70% to about 80%, whereas Alloy No. 2 is preferably present as a minor proportion, i.e., less than about 50% by weight, e.g., about 10% to about 45% by weight, optimally about 20% to about 30%. In an optimal case, the powdered alloys are present in the proportion of about 3 parts of Alloy No. 1 and about 1 part of Alloy No. 2 by weight. Thus, for 100 parts of a complete dental amalgam composition, approximately 75 parts of Alloy No. 1 are mixed with approximately 25 parts of Alloy No. 2.

The term "spheroidal" as used to described the shape, configuration or form of the particulates of Alloy No. 1 in the admixture of the present invention means that the individual particles are spheres or shaped like a spheroid, that is, the particles are approximately spherical, and usually with a relatively smooth surface. A particle is approximately spherical if the largest dimension is no greater than about 130% of the smallest dimension. Processes for producing alloys in spheroidal form are known to those skilled in the art. The term "spheroidal" will be more clearly understood from a consideration of the drawings hereinafter referenced.

The term "irregularly shaped" as used to describe the shape, configuration or form of the particulates of Alloy No. 2 means that the individual particles are substantially multi-sided and generally angularly shaped or rectilinear, albeit irregular, and usually with rough or otherwise relatively non-smooth surfaces. Typically they are in the form of what is variously referred to in the art as microcut material, lathe-cut material, platelets or filings. Conventional microcutting, lathe cutting or filing techniques can be employed satisfactorily to obtain the irregularly shaped particles and are well known to those skilled in the art. The term "irregularly shaped" will be more clearly understood from a consideration of said drawings hereinafter referenced.

The particle size distribution of both Alloy No. 1 and Alloy No. 2 is normally within the range of about 1 to about 100 microns, e.g., about 2 to about 80 microns, preferably about 5 to about 40 microns. The particle size range designation means that substantially all of the particles will pass a sieve or screen having openings corresponding to the larger size and substantially all of the particles will be retained on a sieve or screen having openings corresponding to the smaller size. The average particle size is typically in the range of about 20 to 30 microns, although the invention is not necessarily limited thereto.

To form a dental amalgam composition in accordance with this invention a major proportion of spheroids of Alloy No. 1 and a minor proportion of irregularly-shaped particulates of Alloy No. 2 are mechanically or manually mixed to produce a substantially uniform blend. In the preferred mechanical embodiment, the two alloys are mechanically mixed in a conventional blender for at least about 15 minutes, e.g., about ½ hour to about 1½ hours, typically about 1 hour. For dental use, the complete amalgam admixture is triturated with mercury in amounts of from about 0.8:1 up to about 1.5:1 parts of mercury by weight per part of the alloy powder. Preferably mercury is employed in a ratio of from about 0.9:1 to about 1.4:1 parts of mercury by weight per part of alloy powder, optimally a ratio of about 1:1.

Conventional trituration equipment and techniques may be employed, such as the condensation technique of the American Dental Association Specification No. 1 for dental amalgams. Typically, a one-spill trituration time of about 3–8 seconds at a vibration frequency of about 3,000 to 4,000 cycles per minute may be employed, e.g., about 5 seconds at about 3,500 cycles per minute.

DESCRIPTION OF THE DRAWING

The present invention will be more clearly understood from the accompanying drawing wherein.

Figure 1:
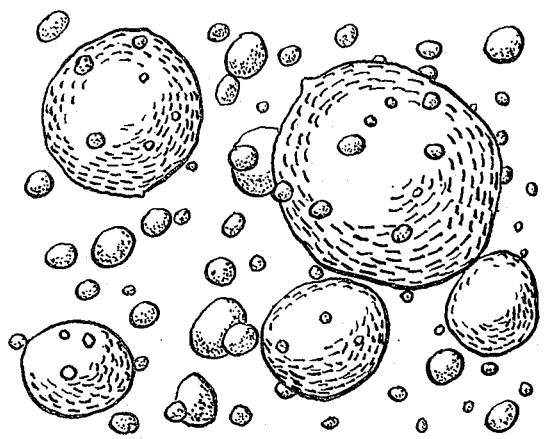
FIG. 1 is a highly magnified illustration of the spheroidal form of the particles of Alloy No. 1 which make up a major proporation of the blended dental amalgam of the present invention.
Figure 2:
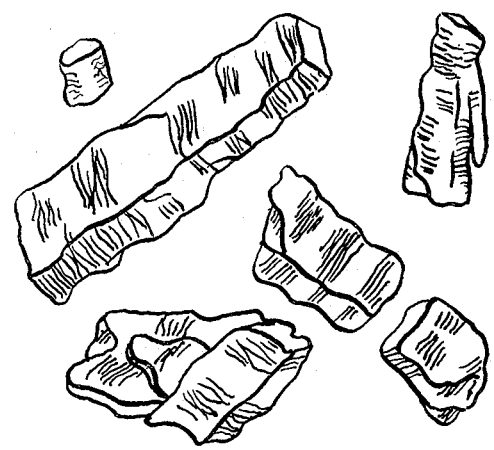
FIG. 2 is a highly magnified illustration of the irregularly-shaped form of the particles of Alloy No. 2 which make up a minor proportion of the blended dental amalgam of the present invention.
Figure 3:
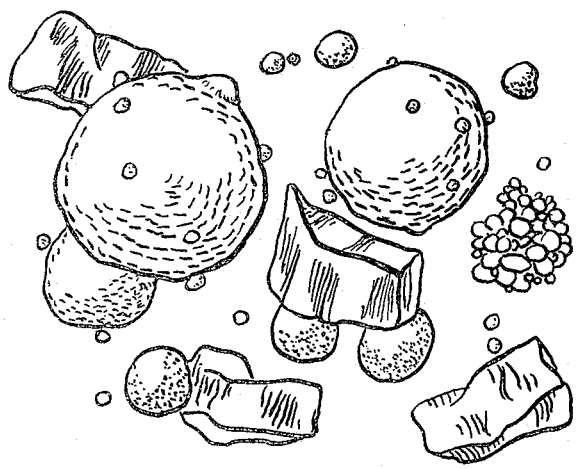
FIG. 3 is a highly magnified illustration of the blended dental amalgam of the present invention prepared by blending particles having the forms illustrated in FIGS. 1 and 2.

The following examples further illustrate the present invention or provide comparative information and data which point up the advantages of the present invention.

EXAMPLE 1

The dental composition of the present invention was produced by mechanically mixing 3 parts by weight of an alloy containing 50% by weight silver, 30% by weight copper and 20% by weight tin in the form of spheroidal particulates having a particle size distribution in the range of about 1 to 100 microns, with 1 part by weight of an alloy containing 68% by weight silver, 27% by weight tin, 4.4% by weight copper and 0.6% by weight zinc in the form of flakes, also having a particle size distribution in the range of about 1 to 100 microns. Mechanical mixing of the two powdered alloys was employed to provide a substantially uniform blend. The resulting powdered dental composition was triturated in conventional manner with mercury using the condensation technique of the American Dental Association Specification No. 1 for dental amalgams, the ratio of mercury to composition being about 0.9:1.

The resulting dental amalgam was subjected to tests to determine physical characteristics, e.g., working time, diametral tensile strength, flow characteristics and dimensional change. The results were as follows:

| Working Time (Minutes) | 15-Minute Diametral Tensile Strength psi | One-Hour Diametral Tensile Strength, psi | Flow Test, % | 24-Hour Dimensional Change microns/cm |
|---|---|---|---|---|
| 4 | 450 | 4,000 | 0.08 | +11.7 |

The amalgam was checked for the presence of the gamma-2 phase. This was done by anodic polarization measurements in saline solution about 24 hours after trituration and condensation, the results being presented in the form of an anodic polarization diagram. Such technique and diagram represents one means of detecting the presence of grandma-2, the indication being a current density peak at about −250 mv(SCE), indicative of the formation of tin oxide or tin oxychloride. The technique is at least as sensitive as X-ray diffraction for the detection of gamma-2 and is further described in the literature, e.g., Journal of Dental Research, Vol. 51, No. 6, November-December 1972, at page 1675 (Copyright 1972 by International Association for Dental Research). The anodic polarization diagram for the amalgam of this example showed no current density peak at −250 mv, indicating its resistance to gamma-2 corrosion.

Further illustrative examples are as follows:

EXAMPLE 2

An amalgamable dental composition in accordance with the invention is prepared by mechanically mixing 4 parts of an alloy composed of 60% by weight silver, 15% by weight tin and 25% by weight copper in the form of spheroidal particulates with 2 parts of an alloy composed of 60% by weight silver, 32% by weight tin, 7% by weight copper and 1% by weight zinc in the form of irregularly-shaped flakes. Both powders have a particle size distribution within the range of about 2 to 80 microns.

EXAMPLE 3

An amalgamable dental composition in accordance with the invention is prepared by mechanically mixing 4 parts of an alloy composed of 55% by weight silver, 18% by weight tin and 27% by weight copper in the form of spheroidal particulates with 1 part of an alloy composed of 64% by weight silver, 29% by weight tin, 4.5% by weight copper and 0.5% by weight zinc in the form of irregularly-shaped flakes. Both powders have a particle size distribution within the range of about 2 to 80 microns.

EXAMPLE 4

An amalgamable dental composition in accordance with the invention is prepared by mechanically mixing 3 parts of an alloy composed of 45% by weight silver, 22% by weight tin and 33% by weight copper in the form of spheroidal particulates with 2 parts of an alloy composed of 62% by weight silver, 33% by weight tin, 4.2% by weight copper and 0.8% by weight zinc in the form of irregularly-shaped flakes. Both powders have a particle size distribution within the range of about 2 to 80 microns.

While it is essential that the dental composition of this invention be in the form of a mixture of particulates of the two alloys when used, and may be supplied in such form when supplied, it should be understood that for distribution purposes the two alloys can be in the form of separate powders which can be admixed by the ultimate user in the required proportions. Alternatively, the two admixed alloys in the required proportions can be pressed into tablet or capsule form for convenience.

While only certain embodiments have been set forth, alternative embodiments and various modification of the embodiments depicted will be apparent from the above description to those skilled in the art. These and other alternatives are considered equivalents and within the spirit and scope of the present invention.

Having described the invention, what is claimed is:

1. A composition adapted for amalgamation with mercury to form a dental amalgam comprising a substantially uniform blend of:
    a. a major proportion by weight of a first alloy in the form of spheroidal particles having a particle size distribution in the range of about 1 to about 100 microns and consisting essentially of about 40% to 70% by weight silver, about 10% to 30% by weight tin, and about 20% to 40% by weight copper; and
    b. a minor proportion by weight of a second alloy in the form of irregularly-shaped particles having a particle size distribution in the range of about 1 to 100 microns and consisting essentially of about 55% to 75% by weight silver, about 20% to 40% by weight tin, about 0.05% to 10% by weight copper and about 0.1% to 2% by weight zinc.

2. The composition of claim 1 containing about 55% to about 90% by weight of said first alloy and about 10% to about 45% by weight of said second alloy.

3. The composition of claim 1 containing approximately 3 parts by weight of said first alloy and 1 part by weight of said second alloy.

4. The composition of claim 1 amalgamated with about 0.8 to 1.5 parts be weight of mercury per part of composition to form a workable dental amalgam.

5. A process for preparing a dental amalgam which comprises triturating the composition of claim 1 with sufficient mercury to form a workable plastic amalgam.

6. A composition adapted for amalgamation with mercury to form a dental amalgam comprising a substantially uniform blend of:
    a. about 70% to about 80% by weight of a first alloy in the form of spheroidal particles having a particle size distribution in the range of about 2 to about 80 microns and consisting essentially of about 40% to 70% by weight silver, about 10% to 30% by weight tin, and about 20% to 40% by weight copper; and
    b. about 20% to about 30% by weight of a second alloy in the form of irregularly-shaped particles having a particle size distribution in the range of about 2 to 80 microns and consisting essentially of about 55% to 75% by weight silver, about 20% to 40% by weight tin, about 0.05% to 10% by weight copper, and about 0.1% to 2% by weight zinc.

7. A process for preparing a dental amalgam which comprises triturating the composition of claim 6 with mercury in the proportion of about 0.8 to about 1.5 parts by weight of mercury per part by weight of said composition to form a workable plastic amalgam.

* * * * *